(12) United States Patent
Asculai et al.

(10) Patent No.: US 6,444,222 B1
(45) Date of Patent: Sep. 3, 2002

(54) REINFORCED MATRICES

(75) Inventors: Samuel Asculai, Toronto (CA); Bruno Giannetti, Bonn (DE)

(73) Assignee: Verigen Transplantation Services International AG, Leverkusen (DE)

( * ) Notice: Subject to any disclaimer, the term of this patent is extended or adjusted under 35 U.S.C. 154(b) by 0 days.

(21) Appl. No.: 09/850,966

(22) Filed: May 8, 2001

(51) Int. Cl.$^7$ .......................... A61K 9/14; A61F 13/00; A61F 2/00

(52) U.S. Cl. ...................... 424/484; 424/422; 424/424

(58) Field of Search ............................. 424/484, 93.21, 424/94.1, 422, 424

(56) References Cited

U.S. PATENT DOCUMENTS

| | | |
|---|---|---|
| 4,424,208 A | 1/1984 | Wallace et al. |
| 4,488,911 A | 12/1984 | Luck et al. |
| 5,007,934 A | 4/1991 | Stone |
| 5,201,745 A | 4/1993 | Tayot et al. |
| 5,837,278 A | 11/1998 | Geistlich et al. |
| 5,965,125 A | * 10/1999 | Mineau-Hanschke .... 424/93.21 |

FOREIGN PATENT DOCUMENTS

WO    96/25961    8/1996

OTHER PUBLICATIONS

Adkisson, et al., 1998, Novel Scaffold–Independent Neo-cartilage Graft for Articluar Repair, ICRS 2nd Symposium International Cartilage Repair Society.

Albrecht, et al., 1998, Circumferential Seeding of Chondrocytes: Toward Enhancement of Integrative Cartilage Repair, ICRS 2nd Symposium International Cartilage Repair Society.

Archer, et al., 1990, Phenotype Modulation in Sub–populations of Human Articular Chondrocytes In Vitro., J. Cell. Sci., 97:361–371.

Aulthouse, et al., 1989, Expression of the Human Chondroycte Phenotype in Vitro, In Vitro Celluar & Developmental Biology, 25:659–668.

Bonaventure, et al., 1994, Reexpression of Cartilage–Specific Genes by Dedifferentiated Human Articular Chondrocytes Cultured in Alginate Beads, Exp. Cell. Res. 212:97–104.

Brittberg, et al., 1994, Treatment of Deep Cartilage Defects in the Knee with Autologous Chondrocyte Transplantation, NE J. Med., 331:889–895.

Davril, et al., 1974, Isolation and Characterization of a highly Cross–linked Peptide from Elastin of Porcine Aorta, FEBS Letters, 43:331–336.

Debelle, et al., 1999, The Structures of Elastins and Their Function, Biochimie, 81:981–994.

Elastin Products Company Catalog, 1997, Elastin Products Company, Owensville, MO 65066.

Hauselmann, et al., 1994, Phenotypic Stability of Bovine Articular Chondrocytes After Long–term Culture in Alginate Beads, J. Cell. Sci., 107:17–27.

(List continued on next page.)

*Primary Examiner*—Thurman K. Page
*Assistant Examiner*—Blessing Fubara
(74) *Attorney, Agent, or Firm*—Morgan, Lewis & Bockius, LLP

(57) ABSTRACT

A reinforced matrix membrane containing one or more scaffold-forming proteins suitable for cell growth and for use in chondrocyte cell transplantation, and method of making same. The scaffold is incubated with the collagen matrix in solutions, colloidal dispersions, or suspensions of stabilizing proteins. The reinforced matrix may be used in tissue engineering, cartilage transplantation, bone and cartilage grafting, healing, joint repair and the prevention of arthritic pathologies.

19 Claims, 3 Drawing Sheets

OTHER PUBLICATIONS

Kempson, et al., 1976, The Effects of Proteolytic Enzymes on the Mechanical Properties of Adult Human Cartilage, Biochemica et Biophysica Acta, 428:741–760.

Kolettas, et al., 1995, Expression of Cartilage Specific Molecules is Retained on Long-term Culture of Human Articular Chondrocytes, J. Cell. Sci., 108:1991–1999.

Manning et al., 1985, Salt Soluble Cross-linked Elastin: Formation and Composition Fibers, Connective Tissue Research, 13:313–322.

Minas, et al., 1997, Chondrocyte Transplantation, Operative Techniques in Orthopaedics, 7:323–333.

Partridge, et al., 1955, The Chemistry of Connective Tissue, Biochemical Journal, 61:11–21.

Roth, et al., 1980, The Intrinsic Tensile Behavior of the Matrix of Bovine Articular Cartilage and its Variation with Age, J. Bone Joint Surg., 62A:1102–1117.

Smith, et al., 1972, Preparation and Properties of Salt–Soluble Elastin, J. Biol. Chem., 8:2427–2432.

Stone, et al., 1997 Surgical Technique for Articular Cartilage Transplantation to Full–thickness Cartilage Defects in the Knee Joint, Operative Techniques in Orthopaedics 7:305–311.

Woo, et al., Biomechanical Properties of Articular Cartilage in: *Handbook of Bioengineering,* Skalak and Chien, eds., McGraw–Hill Book Company, New York.

\* cited by examiner

REINFORCED MATRICES

FIELD OF INVENTION

The present invention relates to a reinforced matrix, and a method to stabilize and reinforce matrices.

BACKGROUND OF THE INVENTION

Injuries to the cartilage of the knee or other joints often result from abnormal mechanical loads which deform the cartilage matrix. The loads applied to the joint can rupture the collagen network in the matrix and decrease the stiffness of the cartilage matrix.

Cartilage injuries are difficult to treat because human articular cartilage has a limited capacity for regeneration once it has been damaged. Type II collagen is the main structural protein of the extracellular matrix in articular cartilage. Type II collagen, similar to other types of collagen, is comprised of three collagen polypeptides which form a triple helix configuration. The polypeptides are intertwined with each other and possess at each end telopeptide regions that provide the cross-linking between the collagen polypeptides. Collagen matrices in their natural state contain numerous cross-linked triple helices and the individual molecules have a molecular weight of about 300,000 daltons. Type II collagen is found almost exclusively in animal cartilage, while other types of collagen are found in animal hides, membranes, and bones.

Excessive degradation of Type II collagen in the outer layers of articular surfaces of joints is also caused by osteoarthritis. The collagen network is accordingly weakened and subsequently develops fibrillation whereby matrix substances, such as proteoglycans, are lost and eventually displaced entirely. Such fibrillation of weakened osteoarthritic cartilage can reach down to the calcified cartilage and into the subchondral bone (Kempson, G. E. et al., Biochim. Biophys. Acta 1976, 428, 741; Roth, V. and Mow, V.C., J. Bone Joint Surgery, 1980, 62A, 1102; Woo, S.L.-Y. et al., in Handbook of Bioengineering (R. Skalak and S. Chien Eds), McGraw-Hill, New York, 1987, pp. 4.1–4.44).

A method for regeneration-treatment of cartilage would be useful for treating arthritis and other joint conditions and could be performed at an earlier stage of joint damage, thus reducing the number of patients needing more extensive procedures, such as artificial joint replacement surgery. With such preventive methods of treatment, the number of patients developing osteoarthritis would also decrease.

Methods for growing and using chondrocyte cells are described by Brittberg, M. et al. (New Engl. J. Med. 1994, 331, 889). Autologous transplants using cells grown with these methods are also disclosed. Additionally, Kolettas et al. examined the expression of cartilage-specific molecules, such as collagens and proteoglycans, under prolonged cell culturing (J. Cell Science 1995, 108, 1991). They found that, despite morphological changes during culturing in monolayer cultures (Aulthouse, A. et al., In Vitro Cell Dev. Biol., 1989, 25, 659; Archer, C. et al., J. Cell Sci. 1990, 97, 361; Hainselmann, H. et al., J. Cell Sci. 1994, 107, 17; Bonaventure, J. et al., Exp. Cell Res. 1994, 212, 97), when compared to suspension cultures grown over agarose gels, alginate beads or as spinner cultures (which retain a round cell morphology) tested by various scientists, such morphologies did not change the chondrocyte —that is, expressed markers such as types II and IX collagens and the large aggregating proteoglycans, aggrecan, versican and link protein did not change (Kolettas, E. et al., J. Cell Science 1995, 108, 1991).

In addition, chondrocyte cells from donors have been grown in vitro to form neocartilage which has been implanted into animals (Adkisson et al., "A Novel Scaffold-Independent Neocartilage Graft for Articular Cartilage Repair," ICRS $2^{nd}$ Symposium International Cartilage Repair Society, Nov. 16–18, 1998). Further, chondrocyte cells have been seeded onto the cartilage surface of osteochondral cores to attempt cartilage regeneration (Albrecht et al., "Circumferential Seeding of Chondrocytes: Towards Enhancement of Integrative Cartilage Repair," ICRS $2^{nd}$ Symposium International Cartilage Repair Society, Nov. 16–18, 1998). Articular surface defects in knee joints have been treated with various cultured chondrocytes (Stone et al., Operative Techniques in Orthopaedics 7(4), pp. 305–311, October 1997 and Minas et al., Operative Techniques in Orthopaedics 7(4), pp. 323–333, October 1997).

U.S. Pat. No. 5,007,934 to Stone is directed to a prosthetic resorbable meniscus formed from biocompatible and bioresorbable fibers. The fibers include natural fibers or analogs of natural fibers. The natural fibers useful in the invention include collagen, elastin, reticulin, analogs thereof, and mixtures thereof. The fibers are oriented in the matrix circumferentially or radially, or alternatively, the fibers may have random orientations. The fiber may be cross-linked, and the matrix optionally may include glycosaminoglycans.

U.S. Pat. No. 5,837,278 —Geistlich et al. describe a collagen-containing membrane which is resorbable and is used in guided tissue regeneration. The membrane has a fibrous face which allows cell growth thereon and a smooth face opposite the fibrous face which inhibits cell adhesion thereon. The membrane product is derived from a natural collagen membrane (that is, from the hide or tendons of calves or piglets) and, although treated, it is described as maintaining its natural structural features. The collagen is purified with alkaline agents to defat the collagen and degrade substances, and then the purified collagen is acidified, washed, dried, degreased, and optionally cross-linked. The fats are saponified. The membrane is described as containing about 95% by weight native collagen. The collagen does not appear to contain a reinforcing protein.

PCT WO 96/25961—Geistlich et al. describe a matrix for reconstructing cartilage tissue which consists of Type II collagen, optionally including crosslinking. In producing the matrix, cartilage is taken from an animal and frozen, subjected to size reduction, dewatered, defatted, washed, and treated with alkaline materials. Non-collagen alkaline soluble proteins are denatured, destroyed, dissolved, and eliminated. Dialysis and freeze-drying are mentioned as possible treatment steps. The matrix material is stamped to form a required shape and then it is sterilized.

U.S. Pat. No. 4,424,208—Wallace et al. describe an injectable collagen implant material comprising particulate cross-linked atelopeptide collagen and reconstituted atelopeptide collagen fibers dispersed in an aqueous carrier. The atelopeptide form of collagen lacks the native telopeptide crosslinking. In the method described in the '208 patent, collagen obtained from bovine or porcine corium (subepithelial skin layer) is softened by soaking in a mild acid; depiliated; comminuted by physical treatment, such as grinding; solubilized by treatment with acid and a proteolytic enzyme; treated with an alkaline solution; and freed of enzyme. The cross-linked gel form of collagen is formed by radiation-induced or chemical-induced crosslinking, such as by addition of glutaraldehyde. The fibrous form of collagen is produced by neutralizing the solution with a buffer, such as $Na_2HPO_4$. Collagen content of the injectable implant comprises 5–30% fibrous collagen and 70–98% of the cross-linked gel form of collagen.

U.S. Pat. No. 4,488,911—Luck et al. describe the formation of collagen fibers free of the immunogenic, telopeptide portion of native collagen. The telopeptide region provides points of crosslinking in native collagen. The fibers, which may be cross-linked, are described for use as sponges, prosthetic devices, films, membranes, and sutures. In the method described in the '911 patent, (non-Type II; Type I and others), collagen obtained from tendons, skin, and connective tissue of animals, such as a cow, is dispersed in an acetic acid solution, passed through a meat chopper, treated with pepsin to cleave the telopeptides and solubilize the collagen, precipitated, dialyzed, cross-linked by addition of formaldehyde, sterilized, and lyophilized. The '911 patent indicates that its disclosed method obtains the atelocollagen form of collagen, free from noncollagen proteins, such as glycosaminoglycans and lipids. Further, it describes that the collagen may be used as a gel to make, for example, a membrane, film, or sponge and that the degree of crosslinking of the collagen can be controlled to alter its structural properties.

BRIEF SUMMARY OF THE INVENTION

In one embodiment, the present invention provides a method for the reinforcement of matrices with an internal scaffold. One embodiment of the present invention is directed to a method for making a collagen-based matrix comprising incubating collagen with one or more scaffold-forming proteins to form a collagen-protein suspension, lyophilizing the suspension to form a fleece-like material, and pressing the fleece-like material into sheets to form a matrix. In one embodiment, the collagen is Type II or Type I/III collagen. Collagen matrices for use in the present invention include those produced from animal sources such as pig, calf, chicken, sheep, goat, kangaroo and others. In one preferred embodiment, the scaffold-forming protein is a hydrophobic non-glycosylated protein, such as elastin or elastin-like peptide.

In another aspect, the present invention includes chondrocytes seeded on a protein reinforced collagen matrix.

DETAILED DESCRIPTION OF THE INVENTION

Figure 1:
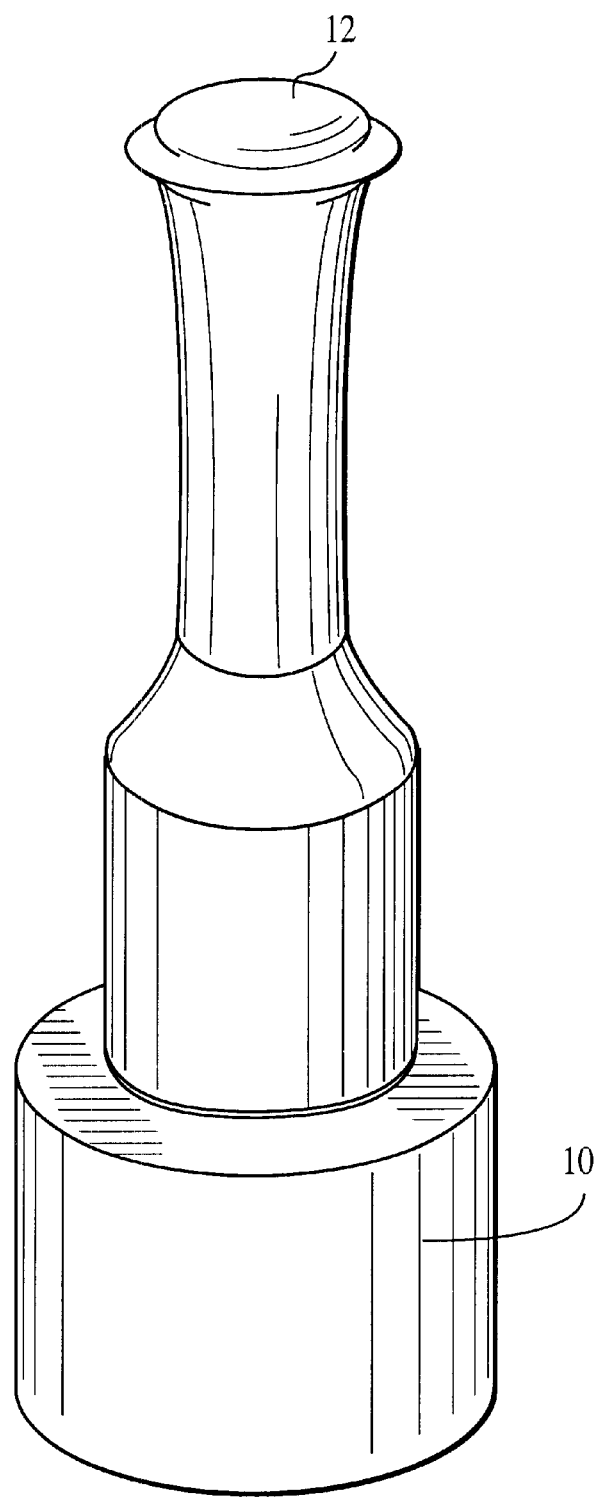
FIG. 1 shows an exemplary pressing device for shaping a reinforced matrix into the sheet-like configuration according to the present invention.

Currently available matrices and membranes having different chemical moieties show a very limited mechanical strength. Most of these matrices or membranes disintegrate after a short period of exposure to cells. Mechanical stability is essential for manipulation of cell-loaded matrices for tissue implantations. In one embodiment, the present invention provides a protein scaffold effective and efficient to reinforce matrices to create new matrices suitable for arthroscopic or other minimal invasive transplantations of chondrocytes or other cells, such as osteoblasts, or mesenchymal stem cells into an area to be treated. The present invention is also directed to polylactic acid and polyglycolic acid reinforcement scaffolds useful in reinforcing matrices.

While analyzing the degradation behavior of different types of collagen materials, it was surprisingly discovered that certain matrix structures were easily degraded by collagenase, but not by trypsin. Other matrix structures demonstrated a significant loss of mechanical strength after treatment with trypsin, but not after treatment with collagenase. In some cases, a combined or subsequent treatment of collagenase and trypsin did not show any significant effect on mechanical strength of the membrane. A subsequent systematic analysis showed that natural, synthetic or semi-synthetic membranes consisting of pure collagen Type I, Type I/III, or Type II structures without or with only a partial cross-linking were susceptible to degradation with collagenase.

Some natural membranes from peritoneum or skin from different animals, such as pigs, sheep, goats, cows, horses, chicken, kangaroos, as well as some commercially available membranes (such as Chondro-Gide® or Chondro-Cell,® from Ed Geistlich Sohne, Switzerland) were found to be quite resistant to collagenase although they contained collagen. Treatment of these membranes with trypsin or trypsin/collagenase, however, showed complete degradation within a certain period of time, that varied in connection with the origin and thickness of the material. These findings suggested the existence of an additional protein scaffold that is not degraded by collagenase and significantly contributes to the mechanical strength and stability of the respective material.

One protein which formed such a scaffold was identified as elastin, however other non-soluble polymeric biodegradable proteins will also work. One example of elastin that can be used in accordance with the present invention is the elastin fractions described by Partridge et al. (Biochem. J. 61: 11–21, 1954), which is hereby incorporated by reference. Specifically, elastin is extracted and purified from the *ligamentum nuchae* of cattle to yield a soluble and substantially pure elastin powder.

In addition, different elastin structures, such as those described by Debelle and Alix (Biochimie 81: 981–994, 1999), which is hereby incorporated by reference, can also be used in accordance with the present invention. Elastin is constituted of globular tropoelastin monomers with substantial amounts of irregular and distorted β-structures. Further, elastin structures are mobile and influenced by the presence of water.

Elastin from different animal species can also be employed. Elastin may be obtained from human, bovine, porcine chicken, sheep, goat, and kangaroo sources.

Elastin-like peptides can also be used, such as those prepared and described by Davril and Han (FEBS Letters 43: 331–336, 1974), which is hereby incorporated by reference. In particular, these porcine elastin-like peptides are enriched desmosine or isodesmosine by enzymatic and chemical digestion of porcine aorta with elastase, themolysin and pancreatic proteases followed by gel filtration, electrophoresis and paper chromatography.

Additionally, salt-soluble elastin can also be used in accordance with the present invention, such as that described by Smith et al. (J. Biol. Chem. 8: 2427–2432, 1972) and Manning et al. (Connective Tissue Res. 13: 313–322, 1985), both of which are hereby incorporated by reference. Salt-soluble elastin can be prepared and purified from porcine aorta by extraction, precipitation and sequential centrifugation or from sheep vascular tissue by hydrophobic interaction chromatography on a column of decyl-agarose.

Treatment of some of the analyzed membranes with different concentrations of elastase lead also to a significant degradation of the analyzed product. Membranes resistant to trypsin, collagenase and elastase were either fully synthetic, such as polyethylenglycol or polyethylenoxide/ polybutyleneterephtalate co-polymers, or were natural and contained additional chemical crosslinking agents.

We demonstrated that incubation of collagen matrices with different quantities of a scaffold forming protein such as elastin significantly increased the mechanical stability of the matrix without affecting the biodegradability of the matrix. Thus, in one aspect, the present invention teaches methods to increase the mechanical strength and stability of collagen matrices and materials using a scaffold forming protein. These reinforced collagen matrices may then be used for a variety of purposes, including cell (e.g., chondrocyte cells) cultivation and implantation.

Suitable matrix materials according to the present invention are characterized as having the ability to enable the growth and attachment of cells such as chondrocytes, and provide a system similar to the natural environment of the cartilage cells. The matrix material is stable for a sufficient period of time to allow full cartilage repair and to be reabsorbed or broken down over time.

Suitable matrix materials include collagen, hyaluronic acid and its derivatives, homologs and analogs; polylactic and polyglycolic acids; polyethylene oxide; and mixtures thereof; fibrin; proteoglycans; proteins and sugars.

Matrix materials for the present invention are prepared from natural sources such as animal skin, peritoneum, or animal cartilage, according to generally accepted and described methods, such as those described in U.S. patent application Ser. No. 09/467,584; U.S. Pat. Nos. 5,201,745 and 5,837,278; and PCT WO 96/25961, all of which are hereby incorporated by reference.

In one such method, the cartilage tissue obtained from the animal is solubilized by physical and/or chemical treatment as described in U.S. patent application Ser. No. 09/467,584, which is hereby incorporated by reference. The solubilization process includes treatment with various buffers to remove impurities and to separate solid and liquid phases; physical treatment to separate solid and liquid phases, such as by centrifugation; and treatment with a proteolytic enzyme to break the crosslinking of the collagen in its telopeptide region into its virtually non-cross-linked atelocollagen, triple helix form.

By reconstituting, it is meant that the non-cross-linked, atelocollagen form of collagen reestablishes its crosslinking between the variable regions along the collagen molecule, including some remaining residues in the telopeptide region. As a result, the collagen loses its liquid or gel-like consistency and becomes more rigid with a higher degree of structural integrity such that cells may be grown upon it.

In another embodiment of the present invention, the collagen matrix is prepared by incubating a matrix with a suspension of elastin, under conditions that will not break down the protein structure. The matrix is prepared under temperature conditions in the range of ambient to 80° C. and under pH conditions in the range of 4–9.

In another embodiment, the matrix composition is formed from recombinantly produced Type II collagen. The substantially pure, recombinantly produced Type II collagen is not cross-linked. However, it can have telopeptide regions. In an embodiment, it is soluble and can be formed into a fleece-like structure.

Matrices for use in the present invention are also commercially available. One material identified as suitable is Chondro-Cell® (a type II collagen matrix pad, Geistlich und Sohne, Switzerland). Another material which may be used in the present invention is Chondro-Gide® (a type I collagen matrix pad, Geistlich und Sohne, Switzerland). Additional matrices for use in the present invention are bovine collagen I/III matrix (Immedex, France) and other matrices such as PermacolTm and various uncross-linked or cross-linked versions thereof, available from Tissue Science Laboratories (UK), and Antema® from Opocrin S.p.A. (Italy) and various universities and institutes. In one embodiment, the matrix has two smooth surface sides, or one smooth surface and one textured or rough surface. A smooth surface on the matrix typically impedes tissue ingrowth, while a textured or rough surface typically promotes cell ingrowth. The surface properties of the matrix may be altered by slowly adding an alcohol, such as ethanol (in a 10–30% solution) in the lyophilization mixture as described in U.S. patent application Ser. No. 09/467,584.

In another embodiment, the consistency of the matrix is fleece-like, and is formed by treating it with one or more cross-linking agents. Cross-linking us also accomplished by heating or subjecting the composition to radiation. The resulting properties of the matrix will vary, but the matrix preferably has a strength in the range of 0.1 to 20 kp, and most preferably in the range of 1.5 to 5 kp.

In one embodiment, the crosslinking agent is an aldehyde-based biocompatible crosslinking agent or a polyvalent aldehyde, such as glutaraldehyde. Also, the crosslinking agent can be a bifunctional agent with two moieties reacting with the support matrix and its components. Examples of the moieties are aldehydes; ketones; acetals; half acetals; moieties which are available for oxidative coupling, such as phenolic groups; quinones, such as flavoids; carboxylic groups; and activated carboxylic acids. Also, ethyldimethyl-aminopropylcarbodiimide (EDC) may be used as a crosslinking agent. Preferred crosslinking agents are chemical compounds containing two aldehyde groups, such as bioflavonoid or cyanidanol, which promote crosslinking by bridging lysine residues on Type II collagen. The type of crosslinking agent to be used is determined by evaluating its effect on the consistency and physical properties of the matrix and its physiological compatibility with the area of the body in which the matrix and cells are to be implanted.

By the term protein scaffold, it is meant an inter-linked, fibrous texture supporting structure such as a three dimensional porous structure comprised of structural proteins. Examples of acceptable scaffold-forming proteins for the present invention include hydrophobic non-glycosylated proteins such as elastin, either in soluble or insoluble form, or elastin-like peptides. Elastin-like peptides include peptides isolated by partial exhaustive hydrolysis of elastin or soluble elastin with different types of elastases, such as pancreatic sputum. In one embodiment of the present invention, the protein reinforced matrix according to the present invention has cells (such as chondrocyte cells) grown thereon to form an implantable article for implanting in animals for repair of an injury or defect, such as cartilage damage.

Chondrocyte cells, which may be autologous or homologous, can be cultured and/or retained on the protein reinforced matrix for use in the treatment of cartilage defects in joints. Chondrocyte cells can be grown directly on the support matrix in standard dishes and/or loaded onto the matrix before use. In use, the chondrocyte cell-loaded protein reinforced matrix, i.e., an implantable article, according to the present invention, preferably is introduced into the joint through an arthroscope, or by minimally invasive or open joint surgery technique. The implantation method of the invention also contemplates the use of suitable allogenic and xenogenic chondrocyte cells for the repair of a cartilage defect.

The cell-loaded protein reinforced matrix is incorporated into various other techniques for effecting or stimulating repair of a bodily defect or damage using various placement and securing devices for implantation. Certain of these techniques and devices are shown in the U.S. Pat. Application of Behrens et al. entitled "METHODS, INSTRUMENTS AND MATERIALS FOR CHONDROCYTE CELL TRANSPLANTATION," Ser. No. 09/373,952, filed Aug. 13, 1999; in U.S. Provisional Application No. 60/096,597, filed Aug. 14, 1998; and U.S. Provisional Application No. 60/146,683, filed August 2, 1999, the entire disclosures of which are incorporated herein by reference.

Thus, the present invention teaches methods and systems for the effective repair or treatment of defects in articular cartilage and bone; osteochondral defects; skin and wound defects; and defects of ligaments, menisci, and vertebral discs. These methods and systems involve the use of an implantable article comprising a protein reinforced matrix of the present invention along with cells, such as chondrocyte cells.

For these purposes, the reinforced matrix of the present invention has a sufficient physical integrity such that it holds a stable form for a period of time to be manipulated for its intended purpose. This strength allows for the growth of cells on the reinforced matrix both before transplant and after transplant, and to provide a system similar to the natural environment of the cells to optimize cell growth differentiation. Over time, perhaps within two to three months, the reinforced matrix is expected to be resorbed in a body of a patient receiving the implant without leaving any significant traces and without forming toxic degradation products. The term "resorbed" is meant to include processes by which the reinforced matrix is broken down by natural biological processes, and the broken down reinforced matrix and degradation products thereof are disposed, for example, through the lymphatics or blood vessels.

GENERAL EXAMPLE

In one embodiment, the reinforced matrix of the present invention is prepared by the following method. Six pieces, each approximately 1 cm² in size of a collagen membrane are incubated with a suspension of elastin in the range of 0.1 mg/100 ml to 100 g/100 ml in a suitable buffer, such as phosphate buffer. The final concentration of elastin in the membrane is between 0.1 mg/100 g to 50 g/100 g. Elastin for use in the present invention is available from EPC, Inc. (USA), specifically sold under the following product numbers: E60, ES60, F65, E61, ES61, E70, ES70, SB77, SB87, SP46, SC55, MT65, ME15, LK215, KE57, K267, ES12, TB872, AE17, BE73, AC27, RA50, MT60, SH476, HA587, HS395, HL457, and HT754. In a preferred embodiment, the phosphate buffer is $KH_2PO_4$. Acceptable pH ranges for the mixture are between about 4.0 and 9.0.

Incubation is performed with suspensions, colloidal dispersions or solutions of a scaffold protein, such as elastin, in different buffers (for example 0.2 m Tris pH 8.8 with 0.1% $NaN_3$ or 0.02M $KH_2PO_4$, pH 7.4) at temperatures between 1 and 102° C. with concentrations of the protein between 0.5 mg/ml and 100 mg/ml.

The above mixture is allowed to coacervate, such as soak, incubate or mix, for 0.05 to 80 hours, preferably about 2 to 8 hours.

The suspension is then lyophilized to obtain a solid. An acceptable temperature range for lyophilization is between about 20° C. and about 60° C., preferably at about 25° C. and at a pressure of about 0.01 to 10 mbar. Lyophilization may be repeated after soaking the product in an aqueous solution, such as with between 10–20 ml of distilled water. The amount of water used will depend upon the size of the lyophilized collagen pellet.

Lyophilization yields a fleece-like material which is then pressed mechanically into sheets for use with cells as an implantation article. The fleece-like material is pressed for a time period of one minute to 48 hours at a pressure of 500 to 1000 grams, preferably at a pressure of 750 grams. A suitable pressing machine for the matrix contains two non-textured stainless steel pieces with bonding material implanted in the pieces. The material is pressed until a sheet-like material that resists tearing upon being handled is obtained.

Figure 2:
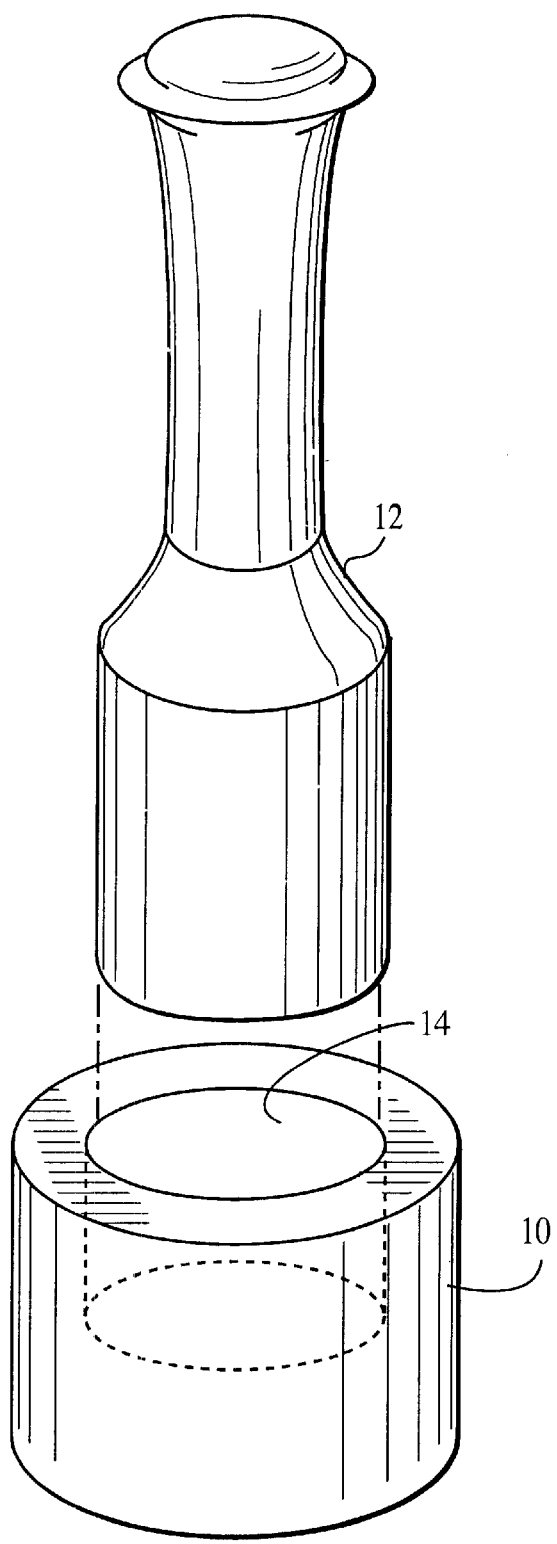
FIG. 2 shows the two components of the exemplary pressing device shown in FIG. 1.

FIGS. 1 and 2 depict an exemplary pressing apparatus which is in the form of two parts and is similar to a mortar 10 and pestle 12. In this embodiment, the pressing apparatus is a stainless steel device with a mortar-like receptacle of approximately 2.5 cm diameter into which a stainless steel pestle-like stamp exactly fits. The matrix material is placed in the mortar-like part and the pestle-like stamp is inserted into opening 14 to apply a mechanical pressing force on the matrix. The pressing device may be any suitable device with enough weight to continually apply force to the matrix. The pressing device preferably is made of stainless steel; however, metals and other materials, for example, plastic, glass, or ceramic, may also be used.

Figure 3:
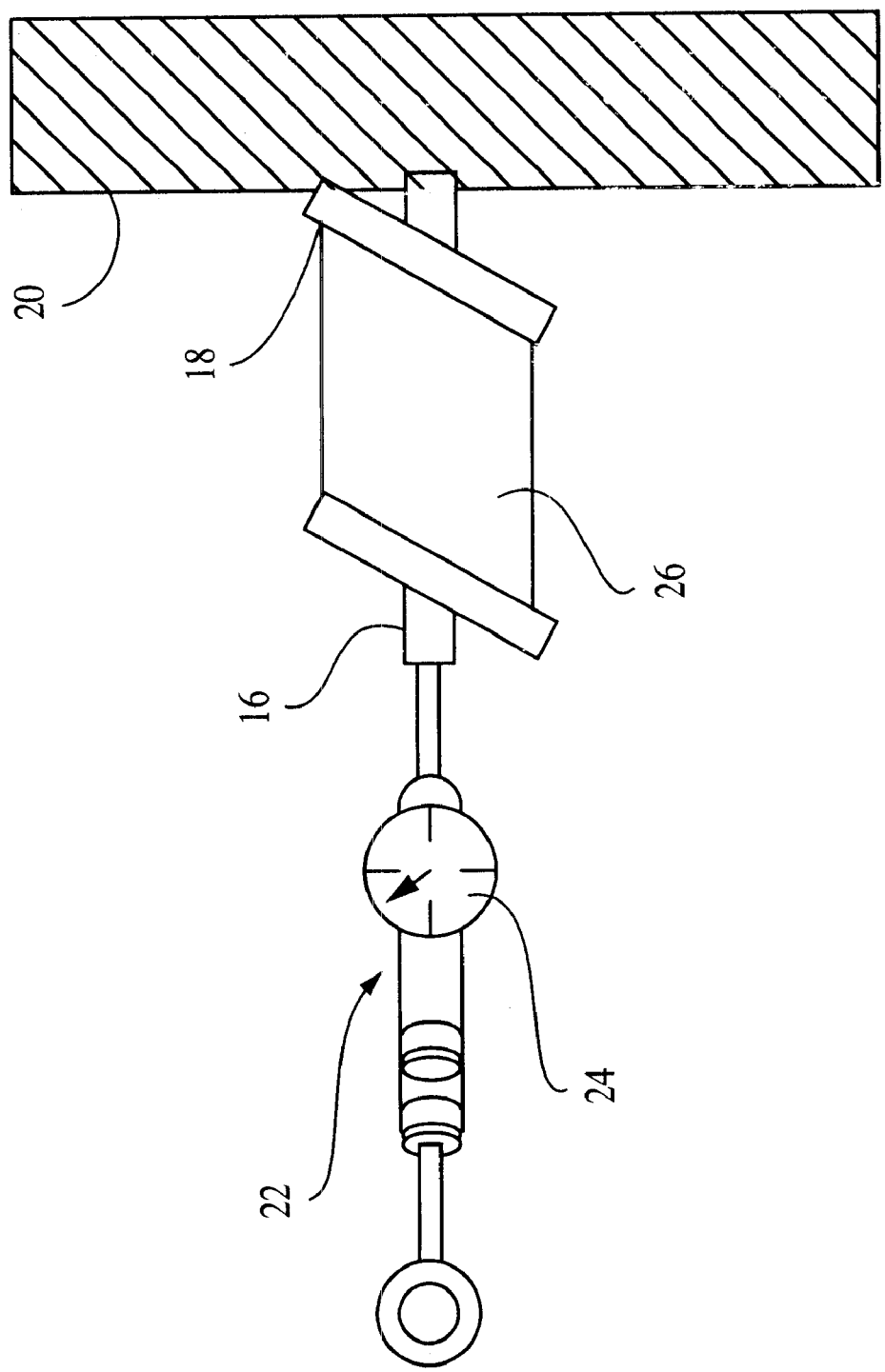
FIG. 3 shows an apparatus for measuring mechanical strength of reinforced matrices according to the present invention.

Mechanical strength of a reinforced matrix according to the present invention, optionally with cells such as chondrocytes grown thereon, is tested by using an in vitro system to study the behavior of the chondrocytes when in contact with the reinforced material. The strength of the chondrocyte-seeded reinforced matrices was then tested against chondrocyte-seeded commercial matrices. In particular, the apparatus shown in FIG. 3 is a preferred method to measuring mechanical strength of the seeded chondrocyte matrices. In use, a reinforced matrix 26 produced according to the present invention is attached to two smooth clamps 16 and 18. Clamp 18 is attached to an immovable surface 20. A calibrated caliper 22 (Ericsen, model number 391–100 II) is attached to clamp 16. Caliper 22 includes a display dial 24 that displays a measure of mechanical resistance at least in the range of 0 to 15 kp. Mechanical strength of reinforced matrix 26 according to the present invention is obtained by applying a pulling force on caliper 22 and observing the level of mechanical resistance reinforced matrix 26 sustains before tearing or breaking down. This in vitro method tests the point of mechanical breakdown of the matrices and predicts the ability of certain materials to mechanically withstand the arthroscopic procedure.

In a preferred embodiment, chondrocytes are grown in culture medium containing one or more suitable buffers and approximately 5 to 7.5% autologous serum in an incubator at 37° C. After a suitable period of time, for example 1 to 14 days, cells are removed from culture and assessed for viability before placing them directly on top of the reinforced matrix material and dispersed over the surface of a cell culture tray. The reinforced matrix is then tested for strength characteristics as described above.

Certain aspects of the instant invention will be better understood as illustrated by the following examples, which are meant by way of illustration and not limitation.

Example 1

Chondrocytes were grown in minimal essential culture medium containing HAM F12, 15mM Hepes buffer and 5 to 7.5% autologous serum in a $CO_2$ incubator at 37° C. and handled in a Class 100 laboratory at Verigen Transplantation Service ApS, Copenhagen, DK. Other compositions of culture medium may be used for culturing the chondrocytes.

The cells were trypsinised using trypsin EDTA for 5 to 10 minutes and counted using Trypan Blue viability staining in a Bürker-Türk chamber. The cell count was adjusted to $7.5 \times 10^5$ cells per ml. One NLNCLON™ plate was uncovered in the Class 100 laboratory.

Six Pieces of a size of 1 cm² each of commercially available collagen I/III fleece (Chondro-Gide®, Geistlich, CH) were placed under aseptic conditions into the bottom of the well in the NUNCLON™ cell culture tray.

Approximately $5 \times 10^6$ of the chondrocytes in 5 ml of the culture medium were placed directly on top of the carrier material and dispersed over the surface. The plate was incubated in a $CO_2$ incubator at 37° C. for three days. After this period the chondrocytes were arranged in clusters and started to grow on the carrier. The chondrocytes could not be removed from the carrier by rinsing it with medium or even by mechanically exerting mild pressure on the matrix. At the end of the incubation period the medium was decanted.

Mechanical resistance of the seeded membrane was tested manually under standard conditions by using a calibrated caliper such as the one shown in FIG. 3 to test the point of mechanical breakdown of the fleece. In this example, the breakdown of the membranes occurred at an average traction of 5.4 kp.

The remaining pieces were incubated with cold refrigerated 2.5% glutaraldehyde containing 0.1 M sodium salt of dimethylarsinic acid. The matrix was stained with Safranin O for histological evaluation.

The breakdown traction measured in this experiment was considered as a baseline for comparison for the other experiments as described below.

Example 2

Chondrocytes were grown in minimal essential culture medium containing HAM F12, 15mM Hepes buffer and 5 to 7.5% autologous serum in a $CO_2$ incubator at 37° C. and handled in a Class 100 laboratory at Verigen Transplantation Service ApS, Copenhagen, DK. Other compositions of culture medium may be used for culturing the chondrocytes.

The cells were trypsinised using trypsin EDTA for 5 to 10 minutes and counted using Trypan Blue viability staining in a Bürker-Türk chamber. The cell count was adjusted to $7.5 \times 10^5$ cells per ml. One NUNCLON™ plate was uncovered in the Class 100 laboratory.

Six Pieces of a size of 1 cm² each of a collagen I/III matrix (Immedex, France) was cut to a suitable size fitting into the bottom of the well in the NUNCLON™ cell culture tray and placed under aseptic conditions on the bottom of the well.

Approximately $5 \times 10^5$ of the chondrocytes in 5 ml of culture medium were placed directly on top of the carrier material and dispersed over the surface. The plate was incubated in a $CO_2$ incubator at 37° C. for 3 days. At the end of the incubation period the medium was decanted.

Mechanical resistance of the seeded membrane was tested manually under standard conditions by using a calibrated caliper as shown in FIG. 3 to test the point of mechanical breakdown of the fleece. In this example breakdown of the membranes occurred at an average traction of 0.3 kp. Mechanical resistance was very low compared to Chondro-Gide® making this material not suitable for arthroscopic surgery purposes.

The remaining pieces were incubated with cold refrigerated 2.5% glutaraldehyde containing 0.1 M sodium salt of dimethylarsinic acid was added as fixative. The matrix was stained with Safranin O for histological evaluation.

Example 3

Six pieces, 1 cm² each in size, of the collagen I/III matrix of Example 2 were incubated for 2 hours at a temperature of 50° C. under gentle stirring with a solution of soluble elastin (EPC Inc., USA) in a suitable buffer such as phosphate buffer (0.02M $KH_2PO_4$, pH 7.4) and the pH value was then brought down to 5.0 by adding acetic acid under gentle stirring. The coacervation reaction was allowed to occur for 5 hours.

The suspension was then lyophilized at a temperature of 25° C. and a pressure of 0.05 mbar.

The lyophilization yielded a fleece-like material which was pressed mechanically using the apparatus in FIGS. 1 and 2 into sheets for use with cells as an implantation article. The material was pressed for about 24 hours until a sheet-like material which resisted tearing upon being handled was obtained.

Six Pieces, each 1 cm² in size, of the fleece matrix were cut to a suitable size fitting into the bottom of the well in the NUNCLON™ cell culture tray and placed under aseptic conditions on the bottom of the well.

Approximately $5 \times 10^5$ of the chondrocytes in 5 ml culture medium were placed directly on top of the carrier material and dispersed over the surface. The plate was incubated in a $CO_2$ incubator at 37° C. for 3 days. At the end of the incubation period the medium was decanted.

Mechanical resistance of the seeded membrane was tested manually under standard conditions by using a calibrated caliper as shown in FIG. 3 to test the strength the fleece. In this example, breakdown of the membranes occurred at an average traction of 4.8 kp. Mechanical resistance was comparable to Chondro-Gide®, thus making this material suitable for arthroscopic surgery purposes.

The remaining pieces were incubated with cold refrigerated 2.5% glutaraldehyde containing 0.1 M sodium salt of dimethylarsinic acid was added as fixative. The matrix was stained with Safranin O for histological evaluation.

Example 4

Six pieces, 1 cm² each, of collagen II membrane (produced according to U.S. patent application Ser. No. 09/467,584) were incubated with a water suspension of insoluble elastin (EPC Inc., USA) at 50° C. with gentle stirring produced by treating a suspension of 20 mg/ml micronised insoluble elastin in a 0.2 m Tris buffer (pH 8.8) with 0.1% Triton X and 0.01% $NaN_3$ in a suitable buffer such as phosphate buffer (0.02M $KH_2PO_4$, pH 7.4) and the pH value was then brought down to 5.0 by adding acetic acid under gentle stirring. The coacervation reaction was allowed to occur for 5 hours.

The suspension was lyophilized. The lyophilization may be repeated after re-soaking with an aqueous solution, such as 10–20 ml of distilled water (depending on the size of the lyophilized collagen pellet) at a temperature between about 20° C. and about 60° C., preferably at about 25° C. and at a pressure of about 0.05 mbar. The lyophilization yielded a fleece-like material which was pressed mechanically using the apparatus shown in FIGS. 1 and 2, into sheets for use with cells as an implantation article. The additional working steps were performed identically as described above in Example 2.

Mechanical resistance of the seeded membrane was tested manually under standard conditions by using a calibrated caliper as shown in FIG. 3 to test the point of mechanical breakdown of the fleece. In this example, breakdown of the membranes occurred at an average traction of 4.1 kp. Mechanical resistance was comparable to Chondro-Gide®, thus making this material as such suitable for arthroscopic surgery purposes.

The remaining pieces were incubated with cold refrigerated 2.5% glutaraldehyde containing 0.1 M sodium salt of dimethylarsinic acid was added as fixative. The matrix was stained with Safranin O for histological evaluation.

Example 5

Six pieces, 1 cm² each, of the same material of Example 2 were incubated with a solution of soluble elastin-like peptides, for example elastin peptides CB573, QP45, RY53 at a concentration of 1 to 200 mg/ml from EPC Inc., USA in a suitable buffer such as phosphate buffer (0.02M $KH_2PO_4$, pH 7.4) and then heated up to 50° C. for four hours under gentle stirring. The suspension was then cooled to 40 to 0° C. and lyophilized. The lyophilization may be repeated after re-soaking with an aqueous solution, such as 10–20 ml of distilled water (depending on the size of the lyophilized collagen pellet) at a temperature between about 20° C. and about 60° C., preferably at about 25° C. and at a pressure of about 0.05 mbar. The lyophilization yielded a fleece-like material which was pressed mechanically into sheets for use with cells as an implantation article.

The sheets of material yielded were tested for tearing resistance by a calibrated caliper as shown in FIG. 3. The membrane was fixed in a frame with the calibrated caliper attached to one side of the membrane. Tension was applied to the membrane by pulling the caliper. Tension was continuously recorded with a qualified gauge. Tensile force at which tearing occurred was recorded. The force was detected to be between 3 and 12 kp depending on the lyophilization conditions, the amount and the properties of the added elastin or elastin-like peptides. Commercially available collagen I/III membranes (Geistlich, CH or Tissue Sciences Laboratories, UK) tore between 1 and 6 kp.

In summary, as shown in Table 1, the protein-reinforced matrices of Examples 3, 4, and 5 exhibited a comparable mechanical resistance to Chondro-Gide® and higher mechanical resistance than the matrix of Example 2 that was not reinforced with a protein.

It will be appreciated by persons skilled in the art that numerous variations and/or modifications may be made to the invention shown in the specific embodiments without departing from the spirit and scope of the invention as described.

TABLE 1

| Example No. | Matrix Conditions | Protein Reinforcement | Mechanical Resistance (kp) |
|---|---|---|---|
| 1 | Chondrocytes on Chondro-Gide | No | 5.4 |
| 2 | Chondrocytes on Immedex membrane | No | 0.3 |
| 3 | Chondrocytes on protein-reinforced Immedex membrane | Yes | 4.8 |
| 4 | Chondrocytes on protein-reinforced collagen II membrane | Yes | 4.1 |
| 5 | Chondrocytes on protein-reinforced Immedex membrane | Yes | 3–12 |

What is claimed:

1. A method for making a reinforced matrix comprising incubating collagen with a scaffold-forming protein to form a mixture;

lyophilizing the mixture to form a fleece material; and pressing the fleece material into sheets to form the matrix.

2. The method of claim 1 wherein the collagen is Type II collagen.

3. The method of claim 1, wherein the collagen is Type I collagen and Type III collagen.

4. The method of claim 1 wherein the scaffold-forming protein is hydrophobic non-glycosylated protein.

5. The method of claim 4 wherein the scaffold-forming protein is elastin.

6. The method of claim 1 wherein the scaffold-forming protein comprises elastin fibers.

7. The method of claim 1 wherein the scaffold forming protein is soluble elastin.

8. The method of claim 1 with pH limit/temperature/time limitations.

9. A reinforced fleece membrane comprising a collagen matrix and a scaffold-forming protein.

10. The membrane of claim 9 wherein the collagen is Type II collagen.

11. The membrane of claim 9 wherein the collagen is Type I collagen and Type III collagen.

12. The membrane of claim 9 wherein the collagen is non-cross-linked.

13. The membrane of claim 9 wherein the collagen is cross-linked.

14. The membrane of claim 9 wherein the collagen is natural collagen.

15. The membrane of claim 9 wherein the scaffold-forming protein is hydrophobic non-glycosylated protein.

16. The membrane of claim 15 wherein the scaffold-forming protein comprises elastin.

17. The membrane of claim 9 wherein the scaffold-forming protein comprises elastic fibers.

18. The membrane of claim 9 wherein the scaffold forming protein is soluble elastin.

19. A composition for implantation or for arthroscopic surgery comprised of chondrocytes and a fleece membrane comprising a collagen matrix and a scaffold-forming protein.

* * * * *

UNITED STATES PATENT AND TRADEMARK OFFICE
CERTIFICATE OF CORRECTION

PATENT NO.    : 6,444,222 B1
DATED         : September 3, 2002
INVENTOR(S)   : Samuel S. Asculai et al.

It is certified that error appears in the above-identified patent and that said Letters Patent is hereby corrected as shown below:

Column 6,
Line 3, please correct where it currently states "a type I collagen matrix pad" to read:
-- a type I/III collagen matrix pad --
Line 6, please correct where it currently states "collagen I/III matrix" to read:
-- collagen I matrix --

Column 9,
Line 12, please correct the spelling of the word "NLNCLON" to read: -- NUNCLON --
Lines 9 and 49, please correct where it currently states "trypsin EDTA" to read:
-- trypsin/EDTA --
Line 55, please correct where it currently states "collagen I/III matrix" to read:
-- collagen I matrix --

Signed and Sealed this

Eighteenth Day of March, 2003

JAMES E. ROGAN
*Director of the United States Patent and Trademark Office*